United States Patent
Elbrecht et al.

(10) Patent No.: US 7,780,654 B2
(45) Date of Patent: Aug. 24, 2010

(54) DEVICE FOR RADIATING LIGHT ONTO A SKIN SURFACE DURING A MEDICAL OR COSMETIC SKIN TREATMENT

(75) Inventors: Jens Elbrecht, Jena (DE); Jan Grieger, Jena (DE)

(73) Assignee: Asclepion Laser Technologies GmbH, Jena (DE)

( * ) Notice: Subject to any disclaimer, the term of this patent is extended or adjusted under 35 U.S.C. 154(b) by 69 days.

(21) Appl. No.: 10/204,351

(22) PCT Filed: Feb. 22, 2001

(86) PCT No.: PCT/EP01/02014

§ 371 (c)(1),
(2), (4) Date: Aug. 20, 2002

(87) PCT Pub. No.: WO01/62340

PCT Pub. Date: Aug. 30, 2001

(65) Prior Publication Data

US 2003/0021124 A1    Jan. 30, 2003

(30) Foreign Application Priority Data

Feb. 23, 2000  (DE) .............. 100 08 977
Apr. 28, 2000  (DE) .............. 100 21 278

(51) Int. Cl.
A61B 18/18  (2006.01)

(52) U.S. Cl. ............. 606/9; 606/13; 606/16; 606/17

(58) Field of Classification Search ........ 606/9, 606/13, 15–17; 607/88, 89
See application file for complete search history.

(56) References Cited

U.S. PATENT DOCUMENTS

| 3,327,712 A | 6/1967 | Kaufman et al. ......... 128/398 |
| 3,622,743 A * | 11/1971 | Muncheryan ............ 607/89 |
| 4,718,416 A | 1/1988 | Nanaumi .............. 128/303 |
| 5,344,434 A | 9/1994 | Talmore |
| 5,395,362 A | 3/1995 | Sacharoff et al. ........ 606/17 |
| 5,688,264 A | 11/1997 | Ren et al. |
| 5,735,844 A | 4/1998 | Anderson et al. ......... 606/9 |
| 5,755,751 A | 5/1998 | Eckhouse .............. 607/88 |
| 5,846,080 A | 12/1998 | Schneider |

(Continued)

FOREIGN PATENT DOCUMENTS

DE    8628810    1/1987

(Continued)

*Primary Examiner*—David Shay
(74) *Attorney, Agent, or Firm*—Leydig, Voit & Mayer, Ltd.

(57) ABSTRACT

The invention relates to a handpiece for radiating light onto a skin surface during a medical or cosmetic skin treatment. An optical coupling element (6) is provided in said handpiece (1). The light entrance surface (8) of said coupling element faces towards a light source, while its light exit surface (5) is in contact with the skin surface (2) during the skin treatment. The invention provides that the coupling element (6) of a handpiece (1) of this type consists of a bundle of light guides which end in the light entrance surface (8) and in the light exit surface (5) and which are in such close lateral contact with each other, at least in their end sections, that there are no optically ineffective intermediate spaces.

10 Claims, 7 Drawing Sheets

U.S. PATENT DOCUMENTS

| | | | |
|---|---|---|---|
| 5,928,223 A | 7/1999 | Shimizu | 606/17 |
| 5,968,033 A * | 10/1999 | Fuller et al. | 606/9 |
| 6,129,721 A | 10/2000 | Kataoka et al. | |
| 6,179,830 B1 * | 1/2001 | Kokubu | 606/16 |
| 6,208,788 B1 * | 3/2001 | Nosov | 606/15 |
| 6,726,681 B2 * | 4/2004 | Grasso et al. | 606/15 |
| 6,735,844 B2 * | 5/2004 | Saccomanno et al. | 29/527.6 |

FOREIGN PATENT DOCUMENTS

| | | |
|---|---|---|
| DE | 4108146 | 9/1992 |
| DE | 4244429 | 7/1993 |
| DE | 19824786 | 1/1999 |
| EP | 0079615 | 5/1983 |
| EP | 0416150 | 3/1991 |
| EP | 0443033 | 8/1991 |
| EP | 0780097 | 6/1997 |
| EP | 0783904 | 7/1997 |
| WO | 9105515 | 5/1991 |
| WO | 9904707 | 2/1999 |
| WO | 9946005 | 9/1999 |
| WO | 9951156 | 10/1999 |

\* cited by examiner

DEVICE FOR RADIATING LIGHT ONTO A SKIN SURFACE DURING A MEDICAL OR COSMETIC SKIN TREATMENT

FIELD OF THE INVENTION

The present invention relates to a device for radiating light onto a skin surface during a medical or cosmetic skin treatment, an optical coupling element being provided in a hand piece of the device whose light entrance surface faces toward a light source and whose light exit surface is in contact with the skin surface during the skin treatment.

The light source can be both a conventional (thermal) light source or a laser radiation source. In this context, the coupling element is mainly used for beam shaping, that is, for influencing the light to be directed onto the skin with regard to the geometric cross-sectional shape of the optical path, the extent of the cross-sectional area and the distribution of the radiation intensity within the optical path at impact on the skin.

BACKGROUND OF THE INVENTION

In the related art, different hand pieces for the most different dermatological treatments with light have become known, the hand pieces being equipped with different means for beam shaping, depending on the particular treatment. Thus, for example, hand pieces for performing the so-called "non-contact technique" are known, in which an optical path which, at least partially, runs in the open atmosphere, is applied to the skin. The optical path is shaped through optics which are also used to influence, for example, to homogenize the intensity distribution within the cross-section of the beam. The optics have a surface which emits the light and is not in contact with the skin during the treatment; the desired spot diameter at the treatment site is changed by varying the distance between the emitting surface and the skin surface, utilizing the radiation divergence.

Another method is known as contact technique in which a transparent optical medium, through which light is passed, is placed onto the skin with its light exit surface. By placing the light exit surface onto the skin, an adaptation of the index to the skin is accomplished, thus preventing that a large part of the energy is scattered back from the skin and is therefore not available for the application.

A hand piece of that kind is connected to a laser radiation source via a light guide device which is so flexible that the hand piece is relatively freely movable, thus allowing the operator to easily direct the laser beam onto the treatment area. Arranged inside the hand piece downstream of the light guiding device is an optical element which is composed, for example, of quartz or of sapphire and features a light entrance surface and a light exit surface that is to be placed onto the skin.

In this context, above all, the relatively large loss of optical power of up to 30% constitutes a disadvantage. The heat loss arising in the process causes problems which, if at all, can only be solved by complex structural measures since dermatological treatments require electromagnetic radiations of relatively high energy.

For the latter reason, as a rule, one endeavors to keep the optical transmission path for the radiation as short as possible, in particular, inside the hand piece. An option in this respect is to integrate the radiation source into the hand piece which, however, results in the disadvantage that the hand piece becomes relatively large and heavy. In this context, the increase in weight is caused, not least, by the measures which are required for cooling. In the case of an integrated radiation source, moreover, it is required for the hand piece to be supplied via power supply and control lines as a result of which its handling is hampered to an unwanted degree.

When diodes are used as laser radiation source in a weight-saving manner and integrated into the hand piece, the disadvantageous effect is produced that the individual laser bars produced by the laser diodes are imaged onto the treatment site and thus homogeneous irradiation of the skin area to be treated is not guaranteed. In this context, it is neither possible to accomplish the desired spot sizes by simply changing an optical element as, for example, by replacing the quartz or the sapphire block in the case of the thermal light source since these are not used here.

An alternative option to the integrated radiation source is to generate the electromagnetic radiation in a separate radiation source which is set apart from the hand piece, and to connect the radiation source to the hand piece via a light guide device. Possible light guide devices include liquid light guides or also bundles of solid light guides. Such light guide devices have the advantage that they can pick up light at a large angle and that they are still flexible even in the case of a relatively large cross-section, allowing nearly unhindered alignment of the hand piece with the skin section to be treated.

Due to the large numerical aperture of such light guides, however, the radiation exits these light guides at very large angles (typically 67° to 80°). In the case of such a large angle of radiation, it is difficult to produce different defined spot sizes having diameters in the range approximately from 5 to 20 mm at the application site because in order to vary the diameter, the distance between the emission-side end of the light guide device and the skin has to be changed in a range of only a few millimeters.

Moreover, not only the spot size but also the intensity distribution within the beam cross-section change very quickly as the distance of the emission-side end from the skin increases. For example, if a light guide has a favorable ratio between diameter and length, a beam profile in the form of a flat top is present at its output. However, this becomes a Gaussian distribution as the distance from the emission surface increases. If the intensity is distributed inhomogeneously over the beam cross-section, overtreatments or undertreatments may result within the treated skin area.

SUMMARY OF THE INVENTION

Starting from this, the object of the present invention is to improve the beam-shaping device inside a hand piece of the type described at the outset in such a manner that the light can be introduced into the skin with high efficiency.

In a hand piece having an optical coupling element whose light entrance area faces toward a light source and whose light exit surface is in contact with the skin surface during the skin treatment, provision is made by the present invention that the coupling element is formed of a bundle of light guides which end in the light entrance surface on one side and in the light exit surface on the other side and which are in such close lateral contact with each other, at least in their end sections, that there are no optically inactive intermediate spaces.

Using a coupling element of that kind, it can advantageously be ensured that the emission-side end of a light guide device or of a light source is imaged onto the skin without having to take any measures for changing the energy distribution within the cross-section of the beam. Unlike when using, for example, a sapphire block composed of a homogeneous body as in known methods heretofore, the coupling element proposed by the present invention for this application is constituted by a plurality of thin individual fibers which are fused together to form a solid rod and which can extend inside the coupling element in an ordered or random fashion. The resolution which can be achieved in this manner is determined by the number and the cross-section of the individual fibers.

In this manner, the previous problems of heat evolution, beam shaping and also of size are solved in a manner that simplifies the design of the hand piece to the greatest extent possible. At this point, it should be pointed out that the contact of the light exit surface with the skin surface can be both an immediate, direct contact and an indirect contact, that is, for example, a thin transparent body such as a film or a small plate can be located between the light exit surface and the skin surface.

Moreover, such a coupling element also allows the external geometrical beam shape to be easily adapted to the requirements of the treatment. Thus, in an embodiment of the present invention, provision is made for the outline and/or the extent of the light exit surface to be different from the outline and/or the extent of the light entrance surface, it being preferred for the light entrance surface to have a circular outline and for the light exit surface to have a square outline. This ensures firstly that the radiation passes from the light guide device, which generally has a circular cross-section, into the light entrance surface (which also has a circular cross-section) in a manner that avoids losses to the greatest extent possible.

If the coupling element is designed in such a manner that the light entrance surface and the light exit surface are equal in shape and extent, the emission-side end of the light guide device is imaged 1:1 onto the skin. However, if, for example, in the design variant of the present invention described above, provision is made for the light exit surface to be larger than the light entrance surface, then the emission-side end of the light guide is imaged onto the skin in a magnified manner. In the opposite case, a reduction results if the light exit surface of the coupling element is smaller than the light entrance surface.

In this context, there is always the advantage that the radiant energy and the intensity distribution present at the light exit surface are essentially identical to those at the light entrance surface, regardless of whether a 1:1 transmission, a magnification or a reduction is accomplished. If the beam profile has a flat top shape at the light entrance surface, then this is also the case at the light exit surface. Thus, if the light exit surface is placed onto the skin according to the contact technique, the radiation acts on the skin with homogeneously distributed intensity.

Preferred embodiments of the present invention provide for the light exit surface to be larger than the light entrance surface, the light entrance surface having a circular outline and the light exit surface having a square outline.

Technologically, a coupling element having such a change in cross-section in the course of its transmission length can be manufactured, for example, in that the plurality of very thin individual fibers in the coupling element are initially fused together to form a solid rod which is then adapted to such a shape in a further manufacturing process. In the process, a tapering rod is formed which is composed of a plurality of individual, also tapering fibers.

It is within the scope of the present invention that the light entrance surface of the coupling element is in immediate communication with one or more light sources, for example, with laser diodes, that are integrated into the hand piece, that is, without an interposed light transmission device. Unlike this, however, a preferred embodiment of the present invention consists in that the hand piece is connected to a light source, preferably a laser light source, via a light guide device which can be composed of liquid guides or fibers, the emission-side end of the light guide device facing the light entrance surface of the coupling element inside the hand piece. Then, the transmission takes place from a circular cross-section at the emission-side end of the light guide device to a circular light entrance surface of the coupling element.

In a very particularly preferred embodiment, the peripheral surface of the coupling element features a truncated-cone-shaped section extending between the light entrance surface and the light exit surface which is coaxially aligned with the center axis and whose tapering end is directed toward the light entrance surface. In this manner, the laser light which is diffusely scattered or reflected back from the skin during treatment and which then re-enters the coupling element through the light exit surface in a direction opposite to the emission direction is prevented from being passed on up to the light entrance surface inside the coupling element, from re-exiting the coupling element only there, and from being absorbed by components of the hand piece in the vicinity of the light entrance surface, which would cause unwanted heating of these components.

This phenomenon is counteracted by the design of the truncated-cone-shaped section proposed by the present invention in that the scattered or reflected light is now no longer passed on from the light exit surface up to the light entrance surface inside the coupling element but is emitted via the peripheral surface of the truncated-cone-shaped section before it reaches the light entrance surface. This takes place so far from the light entrance surface that the scattered or reflected light is kept away from the light entrance surface and thus from the location where the laser radiation to be directed onto the skin for treatment is coupled in, as a result of which the heat evolution cannot occur to an unacceptable degree at this location.

In an embodiment which is further improved in this regard, the truncated-cone-shaped section is provided approximately at half the distance between the light entrance surface and the light exit surface, the peripheral surfaces of the coupling element being designed in such a manner that they extend cylindrically and concentrically relative to the center axis in the region between the light entrance surface and the smaller diameter of the truncated-cone-shaped section and between the larger diameter of the truncated-cone-shaped section and the light exit surface, respectively, and the diameter of the light entrance surface corresponding to the smaller diameter of the truncated-cone-shaped section and the diameter of the light exit surface corresponding to the larger diameter of the truncated-cone-shaped section.

In this context, the circumference of the coupling element in of the region between the light entrance surface and the smaller diameter of the truncated-cone-shaped section can, in some sections, have a diameter which is larger than the diameter of the light entrance surface and larger than the smaller diameter of the truncated-cone-shaped section, respectively, provision being made for tapers toward the light entrance surface and toward the smaller diameter of the truncated-cone-shaped section, respectively.

In this context, the peripheral surface of the coupling element in the area of the truncated-cone-shaped section is, of course, transparent to light that is directed from the inside of the coupling element toward the outside.

In this manner, the disadvantages associated with known methods heretofore as explained further above are eliminated.

In a hand piece having at least one of the aforementioned features, moreover, provision is made by the present invention that a start/stop signal transmitter for the light source is integrated into the hand piece, the start/stop signal transmitter featuring an actuating element which is displaceable essentially in the direction of the exiting radiation of light and which corresponds with the light source via an on-off switch, the switching function "light source off" being given when the hand piece is in the unoperated position; the actuating element being moved after the light exit surface is placed onto the skin while manually increasing the surface pressure between the light exit surface and the skin surface; and the actuating element, when a surface pressure that is predetermined for the treatment is reached between the light exit surface and the hand piece, having moved so far that an automatic changeover from the function "light source off" to the function "light source on" takes place.

As is generally known, the success of a dermatological treatment with light depends on the pressure or surface pressure which is applied to the skin surface to be treated. Thus, given a suitable pressure on the skin, the blood perfusion of the tissue is interrupted, thereby preventing the radiant energy received by the skin from being carried off in the form of heat by the incoming and outgoing blood. The efficiency of the treatment is increased. In the case of a hair-removal treatment, this surface pressure brings all the hair roots located in the treatment zone into one plane, producing a uniform treatment result in the skin region concerned.

Thus, a controlled and successful treatment is accomplished if the energy input into the skin is initiated only when the aforementioned boundary conditions are met, namely, firstly, the contact of the light exit surface with the skin is established (in order to use the flat top shape of the intensity distribution that is still present at the light exit surface) and, secondly, the pressure is exerted on the skin surface to be treated (in order to prevent or reduce the blood circulation in the skin).

Both is achieved through integration of the start/stop signal transmitter proposed by the present invention: To prepare for the treatment, the operator initially places the light exit surface onto the skin region to be treated, initially resulting in a low surface pressure between the light exit surface and the skin which, however, is not optimal for the treatment. When the operator now increases the surface pressure by moving the hand piece in the direction of the skin surface, then a displacement of the actuating element takes place, the surface pressure increasing in proportion to the distance of displacement. When the surface pressure reaches the desired level, the actuating element has moved so far that it acts upon the on-off switch and causes the light source to be switched on since important conditions for the effective treatment are now met.

When the operator removes the hand piece from the skin after the treatment time is over, the surface pressure is removed and the actuating element returns to its unoperated position during which the on-off switch is operated in such a manner that the light sources is switched off.

In an embodiment according to the present invention, the hand piece can be designed such that the actuating element is supported in a straight-line guide and spring-biased in a direction opposite to the direction of placement of the light exit surface, the load-displacement curve of the biasing spring, the extent of the light exit surface to be placed onto the skin and the position of the on-off switch relative to the actuating element being matched to each other in such a manner that the changeover to the function "light source on" takes place when the predetermined surface pressure is reached.

Since dermatological treatments are carried out for different purposes which, for example, require different surface pressures, it is also desirable to be able to perform such different treatments using an adaptable hand piece. In this respect, the present invention can be further developed such that biasing springs having different load-displacement curves and/or coupling elements having different light exit surfaces are available and able to be replaced with each other on the hand piece depending on the parameters to be selected for the different skin treatments (surface pressure, cross-sectional shape of the light exit surface). This allows the hand piece to be used in a versatile manner.

BRIEF DESCRIPTION OF THE DRAWING

In the following, the present invention will be explained the light of an exemplary embodiment. In the associated drawings

DETAILED DESCRIPTION OF THE DRAWINGS

Figure 1:
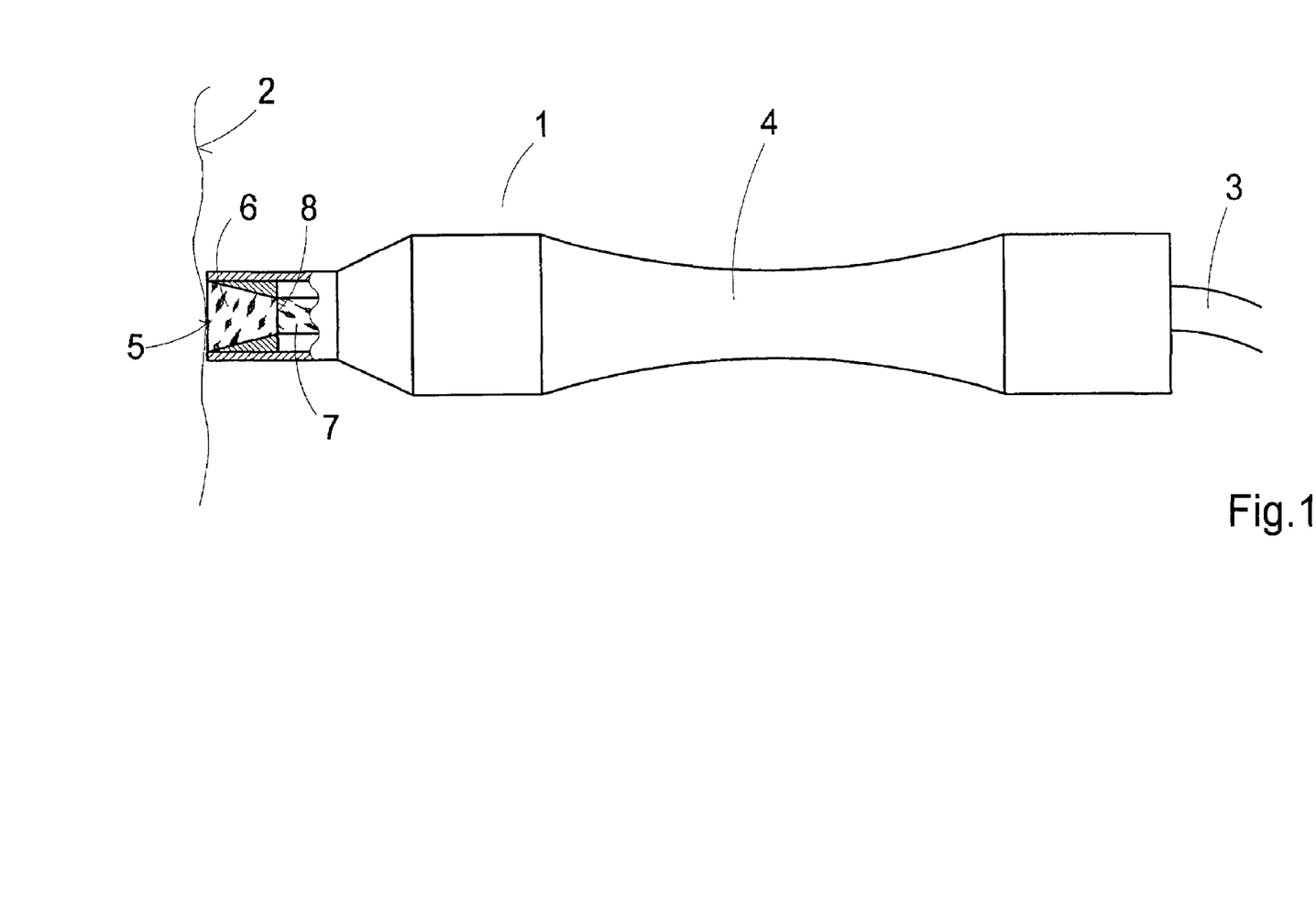
FIG. 1 is an overall view of a hand piece according to the present invention with an integrated coupling element.

FIG. 1 shows a hand piece 1 for radiating light onto a skin surface 2, for example, for the purpose of hair removal. Hand piece 1 is connected to a radiation source (not shown in the drawing) via a light guide device 3, for example, a fiber bundle. It is assumed that a diode laser array is provided as the radiation source.

The hand piece has a grip recess 4 which provides ergonomic handling. During the treatment, the radiant energy is introduced into the skin section to be treated via a light exit surface 5.

During such treatments, it is required that the radiation be introduced into the skin with an energy density that is uniformly distributed over the entire light exit surface 5. Firstly, it is necessary to ensure that the extent of the light exit surface is suitable for the available laser power and, secondly, that the energy is either provided by the light source already in a uniformly distributed manner over the cross-section of the beam or that it is homogenized in the course of the transmission path of the light up to the light exit surface. Often, it is also desirable for light exit surface 5 to have a specific geometrical outline such as a rectangle, a square, a circle, or the like. In this context, in particular, the square shape has the advantage that a plurality of separate skin surfaces can be treated side by side without gaps.

Thus, it is important that the radiant energy be transported from the radiation source to light exit surface 5 as lossless as possible, that the beam be shaped in such a manner that the light is emitted with uniform intensity over entire light exit surface 5 and that, in the process, emission-side end 7 of light guide device 3 is imaged onto the skin surface either in a magnified manner, in a ratio of 1:1, or else in a reduced manner, depending on the structural design. With regard to this, coupling element 6 has a light entrance surface 8 which is located opposite of light exit surface 5 and faces toward emission-side end 7 of light guide device 3.

According to the present invention, provision is made for a coupling element 6 which is formed of a bundle of light guides. These light guides originate in light entrance surface 8 and end in light exit surface 5, from where the radiation is emitted into skin surface 2. In this context, the light guides inside coupling element 6 are in such close lateral contact with each other, at least in their end sections, that optically inactive intermediate spaces are ruled out to the greatest extent possible or, in the ideal case, are not existent.

Figure 2:
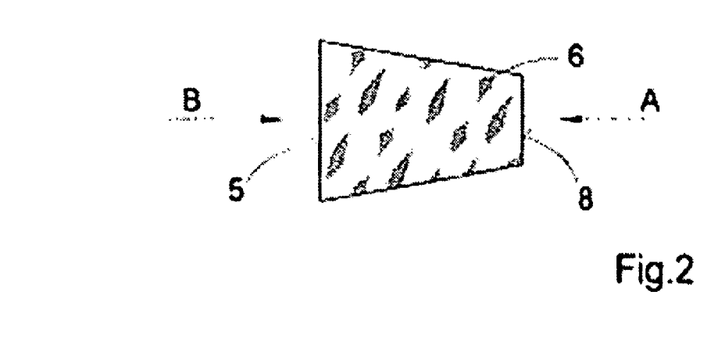
FIG. 2 shows a first embodiment of a coupling element in a separate representation outside of the hand piece with an example of the difference in the cross-sectional shapes of the light entrance surface and the light exit surface.

In other words, according to the present invention, coupling element 6 is formed of a plurality of very thin individual fibers which are fused together to form a solid optical body. The shaping of the beam cross section is accomplished, for example, in that light exit surface 5 has a larger extent than light entrance surface 8, resulting in a coupling element 6 as shown in FIG. 2. In this context, each of the individual fibers inside coupling element 6 has a smaller cross-section at light entrance surface 8 than at light exit surface 5. The greater the number of individual light guide fibers inside coupling element 6, the greater is the resolution which can be attained with the coupling element in the imaging of emission-side end 7 of light guide device 3.

Figure 2A:
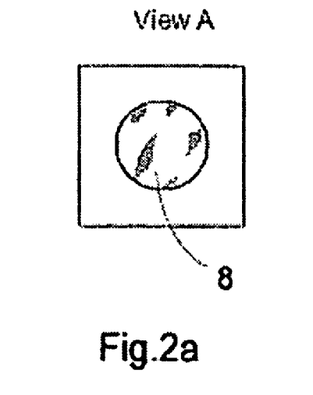
FIG. 2a shows the coupling element according to FIG. 2 in view A.
Figure 2B:
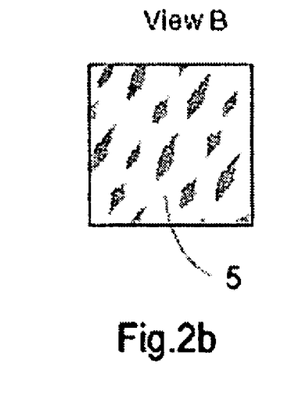
FIG. 2b shows the coupling element according to FIG. 2 in view B.

Coupling element 6 shown in FIG. 2 is a transparent body having a circular light entrance surface 8 and a square light exit surface 5. In this context, FIG. 2*a* depicts light entrance surface 8 in view A and FIG. 2*b* shows light exit surface 5 in view B from FIG. 2. Here too, the fibers forming the transparent body are fused together and, at the same time, are drawn or shaped in such a manner that the cross-section changes from circular to square over the length between light entrance surface 8 and light exit surface 5.

In this manner, the light available at emission-side end 7 of light guide device 3 is advantageously transmitted in a uniform manner via light entrance surface 8 to the square cross-section of light exit surface 5 that is beneficial for the treatment with minimum transmission losses.

Figure 3:
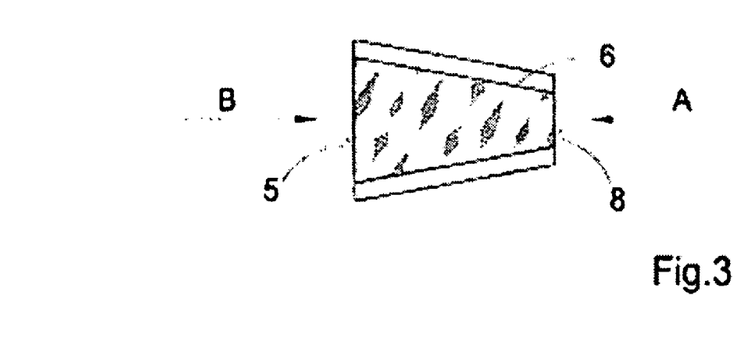
FIG. 3 shows a second embodiment of a coupling element in a separate representation outside of the hand piece with a further example of the difference in the cross-sectional shapes of the light entrance surface and the light exit surface.
Figure 3A:
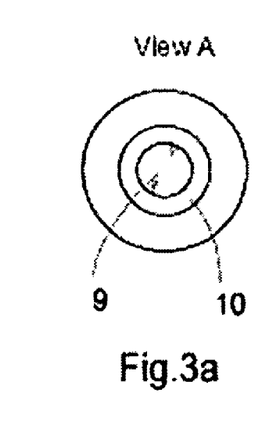
FIG. 3a shows the coupling element according to FIG. 3 in view A.

A further design variant of coupling element 6 is depicted in FIG. 3. Here, the plurality of light guide fibers, which are used to transmit the light from light entrance surface 8 to light exit surface 5, are surrounded by an optically inactive material whose outer shape has the form of a truncated cone. It is visible from FIG. 3*a*, a view A from FIG. 3, that the light guides extending inside the truncated cone fill a circular area 9 in light entrance surface 8 that is surrounded by a ring area 10 of said optically inactive material.

Figure 3B:
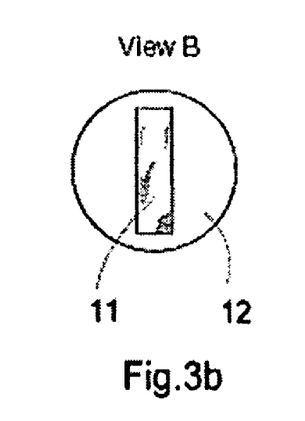
FIG. 3b shows the coupling element according to FIG. 3 in view B.

Light exit surface 5 of this embodiment of coupling element 6 is shown in FIG. 3*b*, a view B from FIG. 3. Here, the plurality of light guides end within a rectangular area 11 which is surrounded by an optically inactive area 12. Here too, the light guides inside coupling element 6 are fused together in such a manner that they fill optically active areas of different size and shape at light entrance surface 8 and light exit surface 5. In this manner, a rectangular spot is made available at light exit surface 5, the energy distribution of which being determined by the position of the individual fibers and their course of from light entrance surface 8 to light exit surface 5.

Figure 4:
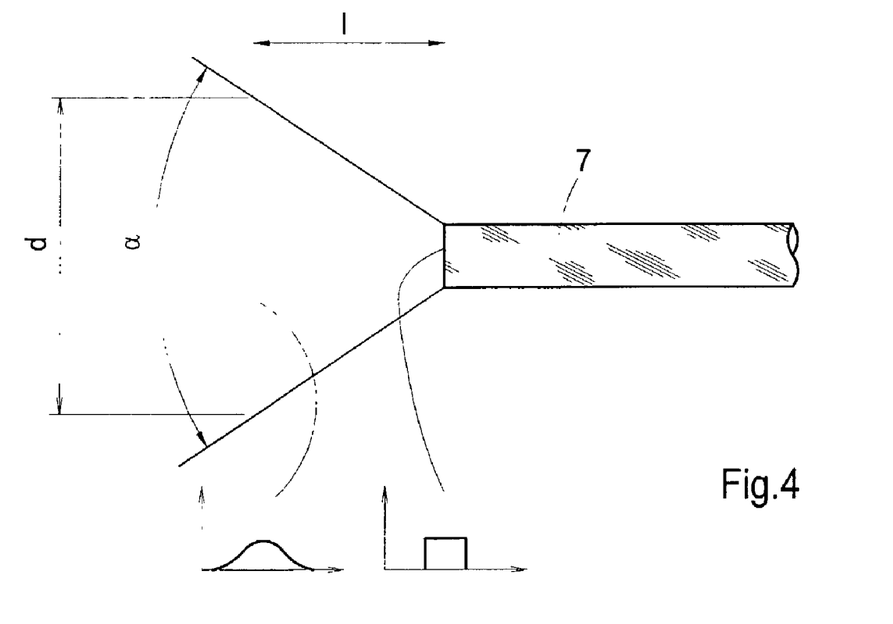
FIG. 4 shows an example of the change in the energy distribution within the beam cross-section with increasing distance from the emission-side end of a light guide having a cylindrical cross-section.

FIG. 4 depicts an example of how the shape and the energy distribution change within a laser radiation which is emitted from emission-side end 7 of a light guide into the open atmosphere. In this context, it is discernible that the light propagates in a cone having a relatively large cone angle $\alpha$ as a result of which, firstly, diameter d of the light spot changes with increasing distance 1 from light exit surface 5 and, secondly, the energy distribution in the light spot having the distance 1 differs from the energy distribution at light exit surface 5.

It is discernible that the radiation exits at light exit surface 5 with a flat top shape while the energy distribution at distance 1 from light exit surface 5 has already a Gaussian shape. If this emission-side end 7 was placed immediately onto the skin, a radiation having a very high intensity and an energy distribution which is uniform over the entire cross-section would be introduced into a relatively small skin surface.

Figure 5:
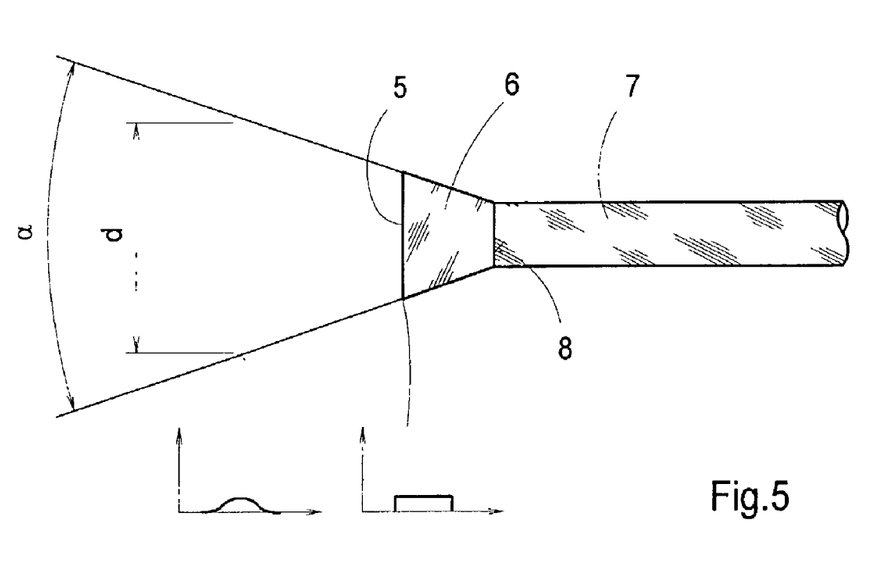
FIG. 5 shows an example of the change in the energy distribution within the beam cross-section with increasing distance from the light exit surface of a truncated-cone-shaped coupling element.

In FIG. 5, however, coupling element 6 is arranged downstream of emission-side end 7, it being achieved by coupling element 6 that the high radiant power at a small beam cross-section is available to provide a radiation at light exit surface 5 that has a larger beam cross-section but, on the other hand, a lower energy density and still a uniform energy distribution, resulting in the advantage that a larger skin region can be gently and carefully treated in a uniform manner.

Figure 6:
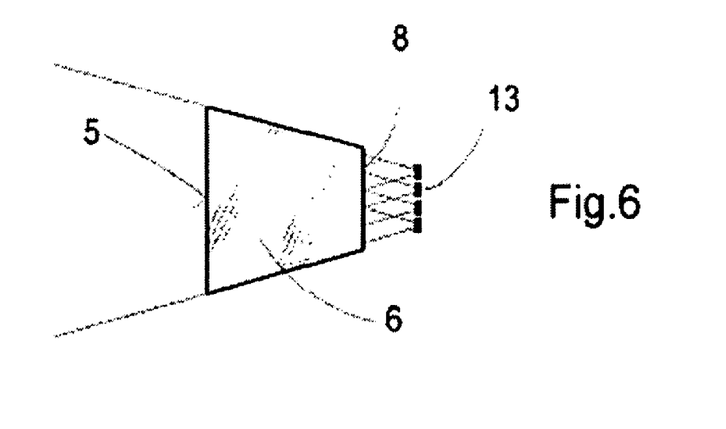
FIG. 6 depicts a coupling element whose light entrance surface is connected to laser diodes inside the hand piece.

FIG. 6 shows an example where the light is not radiated into light entrance surface 8 of coupling element 6 from an end 7 of a light guide device 3 but from a source which is constituted, for example, by an array of laser diodes 13. In this context, the ends of the light guides in light entrance surface 8 can be positioned such that, on one hand, they receive the light of the individual laser diodes 13 in an optimum manner and, on the other hand, emit it at light exit surface 5 in a homogenized manner, the system-related light-to-dark transitions within the laser diode array being able to be compensated for along the course of the light guides inside coupling element 6.

When using a coupling element according to FIG. 5 and FIG. 6, advantageous effects are achieved with regard to the action of the radiation in the depth under skin surface 2, as is described below with reference to FIG. 6*a* and FIG. 6*b*.

Figure 6A:
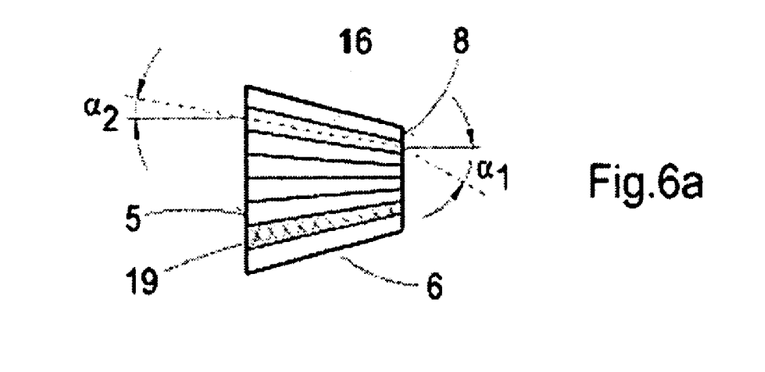
FIG. 6a is an example of the beam guidance inside the individual fibers which form the coupling element.

FIG. 6*a* depicts the principle of radiation reflection inside coupling element 6. Coupling element 6 is assumed to have the shape of a truncated cone. Then, the reflection takes place at lateral surfaces 16 inside all individual fibers 19 of coupling element 6 as is visible from FIG. 6*a*: angle of emergence $\alpha_2$ of a radiation component is smaller than angle of entrance $\alpha_1$ of the same radiation component. In this context, the ratio of angle of emergence $\alpha_2$ to angle of entrance $\alpha_1$ is inversely proportional to the ratio of light entrance surface 8 to light exit surface 5. Individual fibers 19 inside of coupling element 6 are shown here enlarged for reasons of clarity.

In other words: on the light exit side of coupling element 6, the radiation has a distinctly smaller divergence than on the light entrance side. In this manner, a beneficial energy density is achieved at an active depth under the skin surface 2 that is required for a successful treatment, since it is possible to avoid overlaps of spots which are placed side by side and thus, to avoid unwanted overdoses in regions of the skin.

Figure 6B:
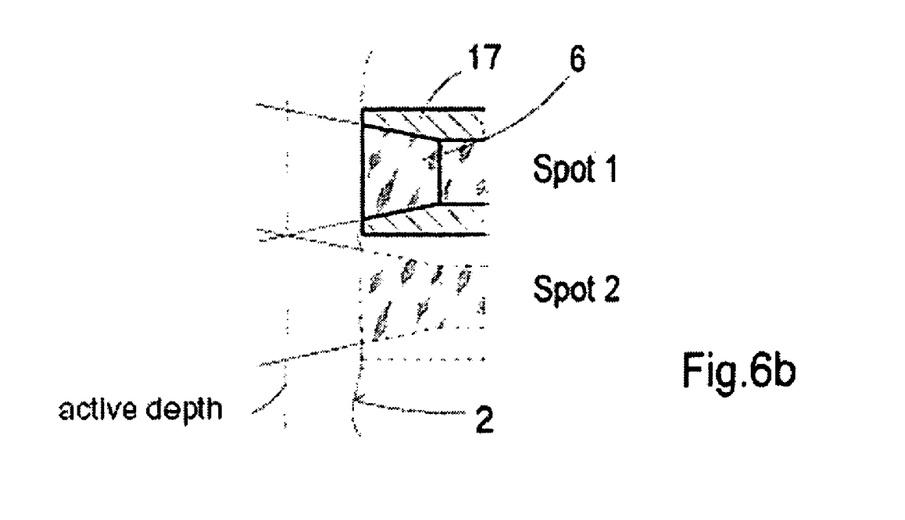
FIG. 6b depicts an example of how the optimum energy density is achieved at the active depth of the radiation under the surface of the skin.

This is shown, by way of example, in FIG. 6b. Here, the outside dimensions of coupling element 6 and the divergence of the radiation penetrating the skin are designed such that the radiation does not overlap at the active depth when placing several spots side by side. Thus, the extent of an optically inactive casing 17 surrounding coupling element 6 can be rated in terms of divergence such that when placed casing 17 from spot 1 to spot 2 on two sections of skin surface 2 which are continuously adjacent to one another, an optimum energy density is achieved at the active depth without overlappings resulting in overdoses and also without any missed spots resulting in an inadequate treatment.

Figure 7:
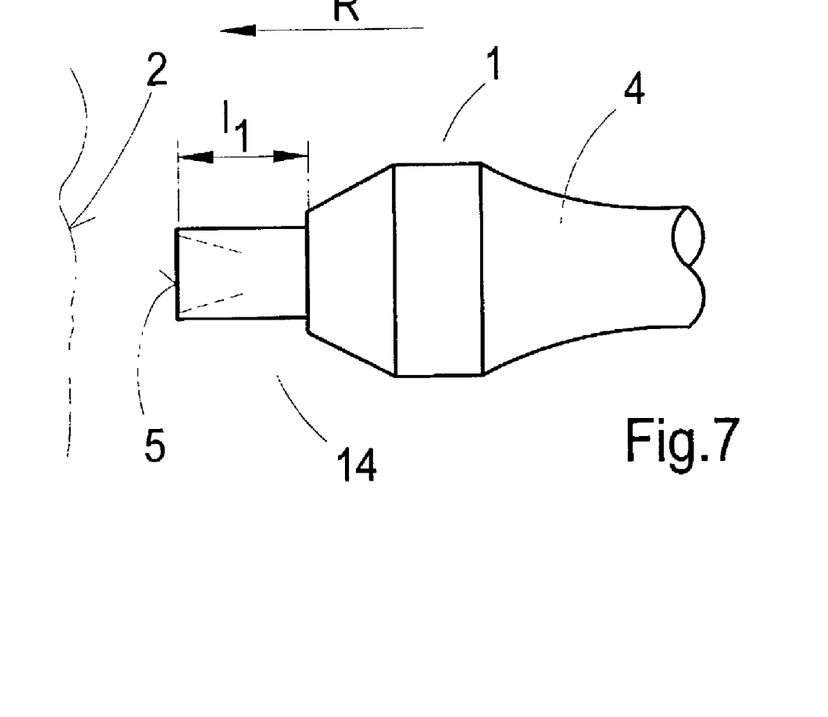
FIG. 7 is a partial view of a hand piece according to the present invention with an integrated start/stop signal transmitter in the operating state "light source off"

FIG. 7 shows a further design variant of the present invention in which a start/stop signal transmitter for the radiation source is integrated into hand piece 1. In this context, provision is made for an actuating element 14 which is displaceable in direction R, which essentially corresponds to the direction of the light emerging from the hand piece. In this connection, actuating element 14 is firmly connected to coupling element 6 but movable relative to the surrounding housing of hand piece 1 in which is formed handle shell 4.

Inside of hand piece 1, actuating element 14 is connected to the radiation source via an on-off switch, the actuating element being supported in a straight-line guide and spring-biased in a direction opposite to direction R. In this context, actuation element 14 is connected to the on-off switch in such a manner that in the situation shown in FIG. 7, in which the treatment is indeed prepared for, but light exit surface 5 has not yet been place onto skin surface 2, the switching function "light source off" is given.

When subsequently light exit surface 5 is placed onto skin surface 2 and thereafter the surface pressure between light exit surface 5 and skin surface 2 is increased to a level that is beneficial for carrying out the treatment by manually exerting pressure in direction R, actuating element 14 is moved into the housing of hand piece 1 as the surface pressure increases, where it corresponds with the on-off switch in such a manner that the changeover to the function "light source on" takes place when the predetermined surface pressure is reached.

In this manner, it is ensured by the present invention that, given a predetermined beam shape, a desired energy distribution within the beam cross-section emerging from light exit surface 5 and, finally, also a sufficient surface pressure between light exit surface 5 and skin surface 2, the laser radiation source is automatically switched on and the treatment is now carried out under optimum conditions.

Figure 8:
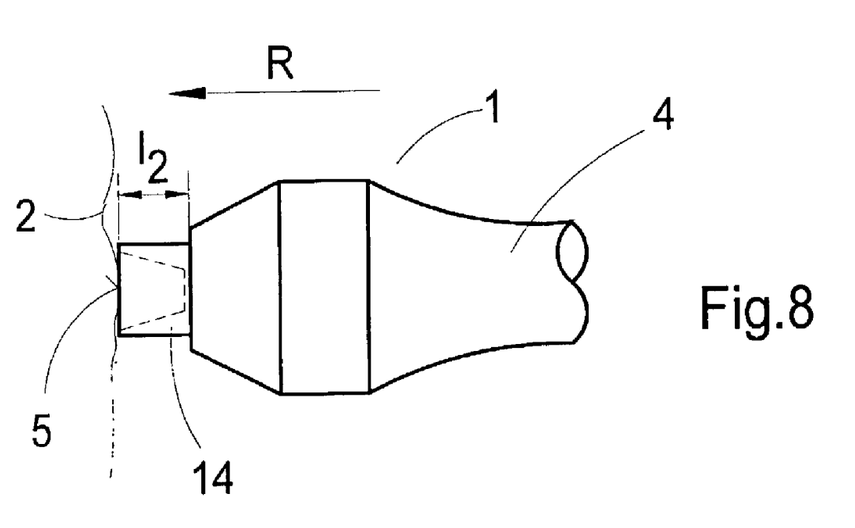
FIG. 8 is a partial view of a hand piece according to the present invention with an integrated start/stop signal transmitter in the operating state "light source on"

This situation is shown in FIG. 8. Here, light exit surface 5 is in contact with skin surface 2 under surface pressure, while distance $I_1$ between light exit surface 5 and the housing of hand piece 1 from FIG. 7 has decreased to distance $I_2$.

The present invention is not limited to the specific embodiment of actuating element 14 that is shown here, but it is also possible to conceive of different embodiments. Thus, for example, actuating element 14 which, both in FIG. 7 and FIG. 8, is designed as a hollow cylinder and accommodates coupling element 6 can be designed in a different manner only as a push-button switch whose end which makes contact with the skin surface is movable relative to light exit surface 5 in direction R.

Moreover, provision can be made for locking elements which prevent actuating element 14 from moving relative to the housing of hand piece 1 so that the operator has the choice of having the light source switched on automatically in the described manner or of switching on the light source himself/herself according to his/her own judgment (for example, via a foot switch), his/her subjective experience in the adjustment of the surface pressure between light exit surface 5 and skin surface 2 being decisive for the operation of the foot switch.

Figure 8A:
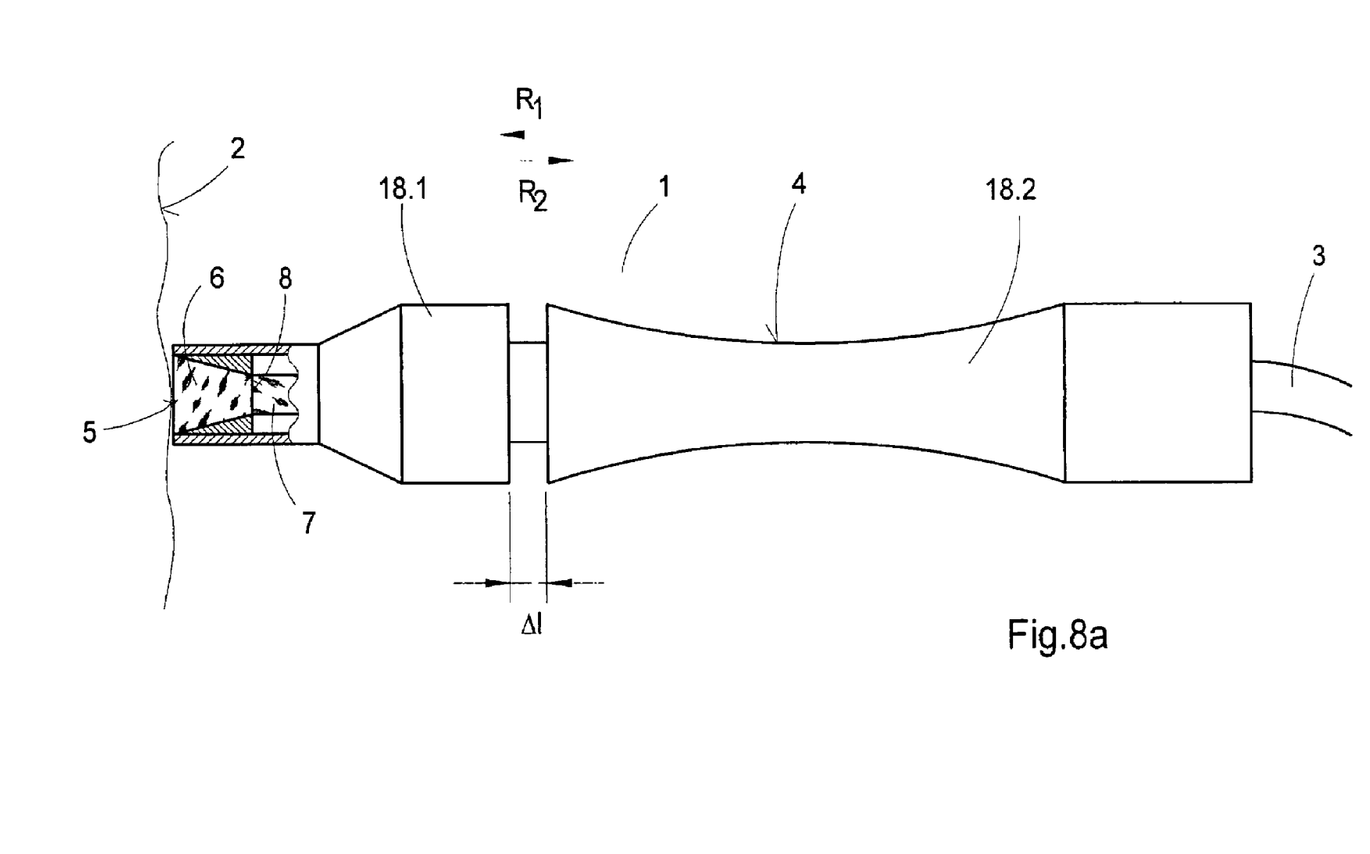
FIG. 8a depicts a further exemplary embodiment of the hand piece according to the present invention.

An embodiment of the present invention as shown in FIG. 8a is also conceivable. Here, hand piece 1 has two grip sections 18.1 and 18.2 which are displaceable relative to each other in the directions denoted by $R_1$ and $R_2$. In this context, grip section 18.1, coupling element 6 and also end 7 of light guide device 3 are firmly connected to one another. Inside of grip section 18.2, light guide device 3 can be supported in such a manner that it is slidably movable.

The two grip sections 18.1 and 18.2 are spring-loaded against each other in displacement directions $R_1$ and $R_2$, respectively, so that the two grip sections 18.1 and 18.2 are adjusted relative to each other to the maximum possible distance $I_{max}$ in direction $R_2$. To this end, for example, a helical spring is accommodated in a cylindrical bore inside hand piece 1 and arranged in such a manner that the preload force is increased when the two grip sections 18.1 and 18.2 are moved toward each other. In doing so, distance 1 changes by the value $\Delta I$ from a maximum distance $I_{max}$ to a minimum distance $I_{min}$. Here too, as already mentioned further above with reference to FIG. 7 and FIG. 8, an on-off switch which is connected to the radiation source is integrated into hand piece 1. This on-off switch is operated when distance 1 is increased or reduced. The actuation of the on-off switch and thus the switching on or off of the radiation source takes place as a function of the characteristic curve of the spring integrated in the hand piece when the spring preload force reaches the values $F_E$ (ON) and $F_A$ (OFF), allowing for a hysteresis.

When treating a skin surface 2, hand piece 1 is grasped in the region of grip section 18.2 at grip recess 4 and placed onto skin surface 2 with light emission surface 5. Grip section 18.2 is moved toward grip section 18.1 which bears against skin surface 2. In the process, the surface pressure between light exit surface 5 and skin surface 2 is increased because of the increasing preload of the spring in the hand piece.

If now change in distance $\Delta I$, spring force $F_E$ and switching instant "ON" are matched to a predetermined surface pressure between light exit surface 5 and skin surface 2, then the radiation source is switched on exactly when this surface pressure is reached. Therefore, the same advantages and the same effect are produced during the treatment as already described in the light of the exemplary embodiment according to FIG. 7 and FIG. 8.

If, in a further embodiment, provision is made for a second manually operated on-off switch which is ORed to the first on-off switch which is integrated in the hand piece, the possibility exists for hand piece 1 to grasped at grip section 18.2 during the treatment, which grip section is firmly connected to coupling element 6. When hand piece 1 is now placed onto skin surface 2, length 1 between the two grip sections 18.1 and 18.2 does not change and therefore the integrated on-off switch is not operated either. The operator can now increase or reduce the surface pressure between light exit surface 5 and skin surface 2 by feeling and according to his/her experience. When the desired contact pressure on skin surface 2 or the supposed optimum surface pressure is reached, the radiation source can be switched on by means of the second on-off switch, which is designed, for example, as a foot switch, and the spot can be placed.

Figure 9:
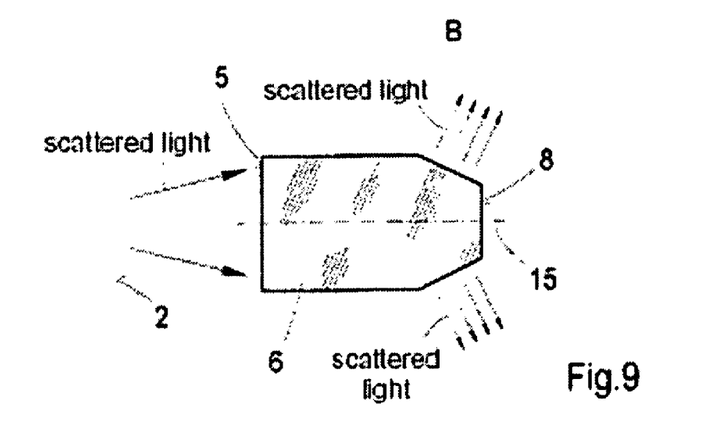
FIG. 9 through FIG. 11 depict different embodiments of the coupling element.
Figure 10:
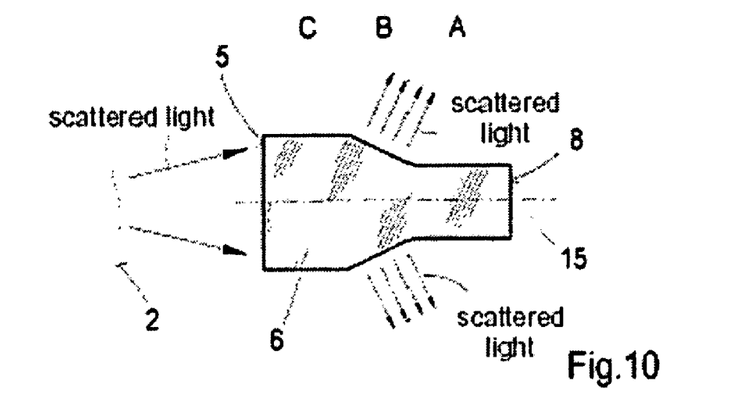
Figure 11:
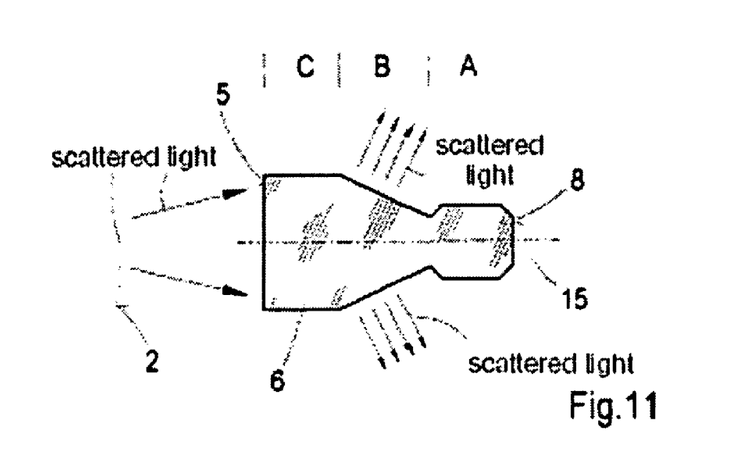

Further examples of advantageous embodiments of coupling element 6 are depicted in FIG. 9, FIG. 10, and FIG. 11.

In the embodiment according to FIG. 9, the coupling element features a truncated-cone-shaped section at its peripheral surface in region B between light entrance surface 8 and light exit surface 5, the cone-shaped section running coaxially with center axis 15 and the tapering end thereof facing toward light entrance surface 8. In this manner, it is ensured that scattered or reflected light which comes from skin surface 2 during the treatment and re-enters coupling element 6 through light exit surface 5 in a direction opposite to the laser radiation directed onto skin surface 2 re-exits coupling element 6 at the peripheral surface of the truncated-cone-shaped section. In this manner, the scattered or reflected light is prevented from reaching light entrance surface 8 and from re-exiting coupling element 6 only there, which would cause this scattered or reflected radiation to be absorbed by mechanical components in the closer vicinity of light entrance surface 8, thus resulting in unwanted heating of these components.

In a further refinement according to FIG. 10, the truncated-cone-shaped section is located approximately at half the distance between light entrance surface 8 and light exit surface 5. In this manner, it is also achieved that the scattered or reflected light entering through light exit surface 5 in an unwanted manner exits at the peripheral surfaces of the truncated-cone-shaped section, region B with the truncated-cone-shaped section being further away from light entrance surface 8 here than in the representation according to FIG. 9.

In this embodiment, provision can be made for both light entrance surface 8 and light exit surface 5 to be circular; region A, which extends between light entrance surface 8 to the beginning of the truncated-cone-shaped section having a cylindrical design. The same applies to region $C_1$ which begins at the truncated-cone-shaped section and extends up to light exit surface 5.

In this context, of course, provision can be made for light exit surface 5 to have a square or otherwise shaped outline, as already described further above, the cross-sectional shape then changing from the circular shape in the region of the transition between regions B and C toward light exit surface 5 into the shape selected for light exit surface 5.

A particularly preferred embodiment of coupling element 6 is shown in FIG. 11. Here, the circumference of coupling element 6 in the region between light entrance surface 8 and smaller diameter $d_t$ of the truncated-cone-shaped section has, in some sections, a diameter which is larger than the diameter of light entrance surface 8 and also larger than smaller diameter $d_1$ of the truncated-cone-shaped section. In this embodiment of coupling element 6, as in the refinement according to FIG. 10, the truncated-cone-shaped section is relatively far away from light entrance surface 8 so that the scattered or reflected light emitted from the inside of coupling element 6 toward the outside is kept away from light entrance surface 8. Thus, in particular, using the embodiment according to FIG. 11, it is achieved in an effective manner that the scattered or reflected light does not reach light entrance surface 8.

While emitting the laser radiation directed onto the skin, coupling element 6 produces a magnification which corresponds to the ratio of light exit surface 5 to light entrance surface 8. If, for example, smaller diameter $d_1$ of the truncated-cone-shaped section is selected to be equal to the diameter of light entrance surface 8 making full use of the numerical aperture of the coupling element, then there is no transmission loss due to the narrowing at small diameter $d_1$ with regard to the laser radiation which is radiated into coupling element 6 through light entrance surface 8. From there, it follows that diameter $d_1$ can also be smaller than the diameter of light entrance surface 8 unless the intention is to make use of the full numerical aperture of coupling element 6. Scattered or reflected light entering coupling element 6 through light exit surface 5 at an angle α which is greater than permitted by the numerical aperture or by the enlargement ratio, is coupled out or emitted outwards at the truncated-cone-shaped section.

What is claimed is:

1. A device for radiating laser light onto a skin surface during a medical or cosmetic treatment comprising:

a laser light source emitting the laser light;

a hand piece including an optical coupling element having a light entrance surface facing toward the laser light source and a light exit surface configured to contact the skin surface during the treatment, wherein the laser light has an intensity distribution with a flat top shape at the light entrance surface and is guided by the optical coupling element from the light entrance surface to the light exit surface so that the intensity distribution of the laser light at the light exit surface has the flat top shape;

the coupling element including a bundle of light guides having end sections ending at the light entrance surface on one side and at the light exit surface on an other side, the light guides being fused together, at least at the end sections, so as to avoid optically inactive intermediate spaces;

wherein the coupling element has a longitudinal axis and a frustum-shaped section disposed between the light entrance surface and the light exit surface centrically to the longitudinal axis, wherein a circumference of the coupling element in a region between the light entrance surface and a smaller diameter of the frustum-shaped section has a diameter that is larger than the diameter of the light entrance surface and also larger than the smaller diameter of the frustum-shaped section, wherein each light guide in the bundle has a smaller cross-sectional area at the light entrance surface than at the light exit surface so that the light exit surface is different from the light entrance surface in geometrical profile and/or circumference, and wherein an angle of emergence of a laser light component from each light guide is smaller than an angle of entrance of the laser light component into the respective light guide.

2. The device as recited in claim 1 wherein the light exit surface is larger than the light entrance surface.

3. A device for radiating laser light onto a skin surface during a medical or cosmetic treatment comprising:

a laser light source emitting the laser light;

a hand piece including an optical coupling element having a center axis and a light entrance surface facing toward the laser light source and a light exit surface configured to contact the skin surface during the treatment, wherein the laser light has an intensity distribution with a flat top shape at the light entrance surface and is guided by the optical coupling element from the light entrance surface to the light exit surface so that the intensity distribution of the laser light at the light exit surface has the flat top shape;

the coupling element including a truncated cone-shaped section disposed between the light entrance surface and the light exit surface, and having a peripheral surface tapering toward the light entrance surface and coaxially aligned with the center axis, wherein the coupling element includes a bundle of light guides each having end sections ending at the light entrance surface on one side and at the light exit surface on the other side, the light guides being fused together, at least at the end sections, so as to avoid optically inactive intermediate spaces, wherein a cross-sectional area of each light guide is larger at the light exit surface than at the light entrance surface, and wherein an angle of emergence of a laser light component from each light guide is smaller than an angle of entrance of the laser light component into the respective light guide, wherein a circumference of the coupling element in a region between the light entrance surface and a smaller diameter of the truncated cone-shaped section has a diameter that is larger than the diameter of light entrance surface and also larger than the smaller diameter of the truncated cone-shaped section.

4. The device as recited in claim 3 wherein the light exit surface has a geometrical outline and/or an extent different from a geometrical outline and/or an extent of the light entrance surface.

5. The device as recited in claim 3 wherein the peripheral surface of the coupling element in the area of the truncated-cone-shaped section is transparent to light directed from an inside of the coupling element toward an outside.

6. The device as recited in claim 3 wherein the light entrance surface has a circular outline and the light exit surface has a square outline.

7. The device as recited in claim 3 further comprising a light guide device having an emission-side end facing toward the light entrance surface inside the handpiece, the light guide device being connected to a laser light source.

8. The device as recited in claim 3 further comprising a laser light source having at least one laser diode integrated into the hand piece.

9. The device as recited in claim 3 wherein the truncated-cone-shaped section is provided at half the distance between the light entrance surface and the light exit surface and has a smaller diameter at one end and a larger diameter at another end, the peripheral surface including another section cylindrical and concentric relative to the center axis in a region between the light entrance surface and the smaller diameter of the truncated-cone-shaped section, a diameter of the light entrance surface corresponding to the smaller diameter of the truncated-cone-shaped section and a diameter of the light exit surface corresponding to the larger diameter of the truncated-cone-shaped section.

10. The device as recited in claim 9 wherein in a region between the light entrance surface and the smaller diameter of the truncated-cone-shaped section, the circumference of the coupling element has a further diameter larger than the diameter of the light entrance surface and larger than the smaller diameter of the truncated-cone-shaped section, the further diameter tapering toward the light entrance surface and toward the smaller diameter of the truncated-cone-shaped section.

* * * * *